(12) United States Patent
Dobetti

(10) Patent No.: US 6,596,311 B1
(45) Date of Patent: Jul. 22, 2003

(54) FAST DISINTEGRATING TABLETS

(75) Inventor: Luca Dobetti, Trieste (IT)

(73) Assignee: Eurand International S.p.A. (IT)

( * ) Notice: Subject to any disclaimer, the term of this patent is extended or adjusted under 35 U.S.C. 154(b) by 0 days.

(21) Appl. No.: 09/623,651

(22) PCT Filed: Mar. 4, 1999

(86) PCT No.: PCT/EP99/01395

§ 371 (c)(1),
(2), (4) Date: Sep. 6, 2000

(87) PCT Pub. No.: WO99/44580

PCT Pub. Date: Sep. 10, 1999

(30) Foreign Application Priority Data

Mar. 6, 1998 (EP) .............................. 98104035

(51) Int. Cl.$^7$ .............................. A61K 9/20; A61K 9/00
(52) U.S. Cl. ........................ 424/464; 424/400; 424/443; 424/468; 424/469; 424/470; 424/489; 514/960
(58) Field of Search ................................ 424/400, 443, 424/464, 468, 469, 470, 489; 514/960

(56) References Cited

U.S. PATENT DOCUMENTS

| 4,866,046 A | * | 9/1989 | Amer ........................ 514/159 |
| 5,720,974 A | * | 2/1998 | Makino et al. ............. 424/464 |
| 5,776,491 A | * | 7/1998 | Allen, Jr. et al. ........... 424/465 |
| 5,869,098 A | * | 2/1999 | Misra et al. ................ 424/465 |

* cited by examiner

Primary Examiner—Thurman K. Page
Assistant Examiner—Charesse L. Evans
(74) Attorney, Agent, or Firm—Thompson Hine LLP

(57) ABSTRACT

This invention provides a formulation for preparing a fast disintegrating tablet comprising a drug in multiparticulate form, one or more water insoluble inorganic excipients, one or more disintegrants, and optionally one or more substantially water soluble excipients, the amounts of said ingredients being such as to provide a disintegration time for the tablet in the order of 75 seconds or less, typically 30 seconds or less.

14 Claims, No Drawings

FAST DISINTEGRATING TABLETS

This invention relates to fast disintegrating tablets and particularly to tablets which not only disintegrate rapidly but also have good friability characteristics.

The tablets of this invention are particularly suitable for rapidly releasing a water soluble or water insoluble drug in granular or microencapsular form, e.g where the drug is for controlled, sustained or targeted release, or where the drug requires gastric protection or taste masking, etc.

BACKGROUND OF THE INVENTION

Over the past years, coated multiparticulate dosage forms have become increasingly important in the development of both controlled release and taste masked pharmaceutical formulations.

Among the variety of coating technologies, microencapsulation is widely recognised as a versatile technique for the coating of particles of active drugs to enhance their therapeutic value. Microencapsulation is achieved by two distinct processes, namely coacervation/phase separation and air suspension coating. These processes envelop small particles of the drug substance into minute, discrete, solid packages which to the naked eye appear as a fine powder.

Although in the marketplace there are many different solid dosage forms for peroral administration containing microencapsulated drugs, such as tablets, capsules, sachets, etc., presently there is a strong demand for multiparticulate palatable dosage forms characterised by a rapid disintegration time.

Such solid oral dosage forms are particularly advantageous for applying large single doses orally, since a tablet or other shaped form can be difficult to swallow especially for patients such as children and the elderly. These problems can be exacerbated when no water is available.

Chewable tablets containing coated particles of active drugs are a well-known dosage form (see for instance the textbook "Pharmaceutical dosage form—tablets" Vol. 1 edited by H A Lieberman et al. Marcel Dekker, Inc. (1989).

They are intended to disintegrate in the mouth under the action of chewing and typically they are larger than tablets which are intended to be swallowed. Advantages over dosage forms for swallowing include improved bioavailability through the immediate disintegration, patient convenience through the elimination of the need for water and patience acceptance through their pleasant taste.

Nevertheless, a common problem of chewable tablets is that chewing can cause a breakdown of the membrane that coats the active particles. Furthermore, the extent of mastication, which is associated with the length of time in which a drug remains in the mouth, plays an important role in determining the amount of taste masking. As a result, the drug's unpleasant taste and throat grittiness are often perceived by the patient.

To overcome such problems, other solid dosage forms known as fast dispersing or disintegrating tablets have been developed. Fast disintegrating tablets containing particles of active are based on the presence of one or more disintegrating agents which allow the tablet, when taken up by mouth, to disgregate quickly into many coated cores of active. However the presence of such ingredients tends to weaken the tablet's structure leading to poor friability values.

Accordingly, fast disintegrating tablets have suffered from problems due to their limited physical integrity as evidenced by their high friability compared to the conventional tablet forms. Thus fast disintegrating tablets have previously been found to fracture or chip easily and therefore require careful packaging and handling prior to placing them in the mouth. Generally as well as disintegrating agent, such tablets may also contain other pharmaceutical ingredients for example swelling agents or thickening agents which are responsible for producing, when the tablets disintegrates directly in the mouth or in a glass of water, a viscous medium that facilitates the suspension of the solid particles. As a result, the total weight of the fast disintegrating tablets can be rather high; thus such dosage forms are generally less acceptable to a patient especially when high dosage of active is required.

Freeze drying processes have been used to prepare fast disintegrating dosage forms. Depending on the manufacturing process, the product obtained is characterised by a solid dried highly porous microstructure of the soluble supporting agent (i.e. mannitol, glycine, lactose, gelatins, etc) in which the active is homogeneously dispersed. Although this technology produces a product which rapidly disintegrates in water or in the oral cavity, a drawback is represented by the poor physical integrity of its physical structure which severely limits further manufacturing operations such as forming blister packs.

Another significant drawback of the freeze drying technology in manufacturing such dosage forms is the high production costs because of the lengthy duration of each freeze drying cycle (normally from 24 to 48 hours). The complexity of the industrial plants is another important factor which prejudices the large scale use of this technology for the development of rapid disintegrating tablets. Moreover, the thermal shocks, as a direct consequence of each freeze drying cycle, might physically modify the physical-chemical properties of the outer membrane of microencapsulated particles.

There is a need therefore for a compression tablet with fast disintegrating properties and satisfactory structural integrity and especially such a tablet having a rapid disintegration time when taken by mouth (e.g. within 45–40 seconds, preferably within 30 seconds and most preferably 20 seconds or less). There is a need for a fast disintegrating tablet that is small for improved patient acceptability without reducing the clinical performance.

There is also a need for a fast disintegrating tablet (such as a tablet which disintegrates in the mouth in 75 seconds or less) having an enhanced structural integrity, for instance having a friability lower than 2.0% according to USP XXIII test; preferably lower than 1.5% and most preferably 1.0% or lower.

Further there is a need for a fast multiparticulate disintegrating tablet that can be produced on industrial scale with a simple manufacturing process based on a direct compression method of a mixture of selected ingredients.

There is also a need for a fast disintegrating tablet preferably having an extremely short disintegration time, quantifiable in less than 20 seconds, when taken directly by mouth without water and without the necessity of chewing the tablet and wherein the active is in the form of microcapsules having controlled release and/or gastro-resistance and/or taste masking properties.

Advantageously any multiparticulate fast disintegrating tablet should possess a physical integrity approaching that of a conventional tablet without limiting the disintegration performance of the tablet.

We have surprisingly found that by careful selection of ingredients, it is possible to prepare fast disintegrating tablets using conventional tableting means that have either disintegration rates which are faster than previously known tablets or show superior friability properties, or both. Furthermore we have been able to prepare fast disintegrating tablets without the need to use substances which effervesce on contact with water.

It has now been found that the above-mentioned drawbacks of previous tablets may be overcome by using a dry mixture of pharmaceutically acceptable excipients in selected amounts. This mixture comprises at least one water insoluble inorganic excipient and at least one disintegrant in appropriate amounts and optionally combined with one or more water soluble constituents.

We have surprisingly found that the disintegration time of tablets having satisfactory mechanical properties (such as hardness and friability), when placed in the oral cavity depends not only on the quantity of disintegrant used, but also on the quantity of the insoluble inorganic excipient and if present soluble excipient and the relative weight ratio between these components (disintegrant, insoluble excipient and drug and if present soluble excipient).

As a result disintegration can occur in less than 20 seconds with the disintegration occurring exclusively under the action of the components (i.e. chewing is not required). Tablets are obtained by mixing the components of the solid mixture in powdery form, (where the active is in the form of coated or uncoated particles) and directly applying compression forces to produce tablets having enhanced physical integrity without affecting their excellent disintegration properties.

By optimising the disintegrant's performance, it is also possible to get a total weight decrease of the finished dosage form in comparison for instance with those produced with different technologies and characterised by a similar disintegration time. No other prior art approach, based on direct compression, attains these beneficial results.

Accordingly this invention provides a fast disintegrating tablet comprising a drug in multiparticulate form, e.g. granular or microencapsulated; one or more water insoluble inorganic excipients, one or more disintegrants; and optionally one or more substantially water soluble excipients, the amounts of said ingredients being such as to provide a disintegration time in the mouth in the order of 75 seconds or less, eg. 40 seconds or less, preferably less than 30 seconds, most preferably less than 20 seconds.

We have also found that it is possible to apply sufficient compression when forming the tablet to produce tensile strengths which impart the desired characteristics such as low friabilty without adversely affecting disintegration rates.

Friability is an index which provides a measure of the ability of a tablet to withstand both shock and abrasion without crumbling during the handling of manufacturing, packaging, shipping and consumer use. As a means of controlling and quantifying the measurement of friability, a laboratory device known as Roche friabilometer, is routinely used. The method to determine such measurement refers to both USP XXIII and European Pharmacopoeia prescriptions. Conventional tablets that lose less than 0.5 to 1.0% in weight are generally considered particularly acceptable. Of course, depending on their physical characteristic, fast disintegrating tablets previously known have higher friability weight losses.

Accordingly a further aspect of this invention provides a tablet adapted to disintegrate in less than about 75 seconds , preferably 40 seconds or less comprising a drug in multiparticulate form, e.g. granular or microencapsulated; one or more water insoluble inorganic excipients; one or more disintegrants; and optionally one or more substantially water soluble excipients, the amount of said ingredients and the tensile strength of the tablet being such that the tablet has a friability value less than 2%, preferably less than 1.5% most preferably about 1% or less.

The drug used is preferably substantially water insoluble or is coated with an outer substantially water insoluble membrane or layer which protects/isolates the active at least through the mouth and throat and if required through the stomach or through the stomach and the small intestine. The coated or uncoated microparticles of the drug may typically have a particle size distribution ranging from approximately 20 to about 1000 microns. Average particle size can be for example 120 to 150 microns or more, eg. 200 microns. In order to produce a palatable mouth feel without grittiness, microparticles with a maximum particle size lower than 700 microns are preferred. Coated microparticles of active drug can be obtained through various well known technologies such as for instance, but not limited to, phase separation and fluid bed coating. Coated microparticles having taste masking properties are preferably obtained by phase separation (coacervation) since this process ensures the most uniform coverage of a drug substance.

Uncoated microparticles of active include substantially water insoluble particles which can be produced for instance by well known technologies such as dry granulation, wet granulation, melt granulation, direct pelletization with a rotor granulator and extrusion spheronisation.

The amount of coated or uncoated multiparticulate drug is generally 14% or more of the tablet weight depending on the active and can be up to 75% or more. Typical ranges of coated or uncoated active are from 20% to 70% by weight of tablet. For actives such as ibuprofen, preferred ranges are from 40% to 60%.

Disintegrating agents suitable for use in the present formulations include pharmaceutical excipients which facilitate the break-up of a tablet when it is placed in aqueous environment. Disintegrants once in contact with water, swell, hydrate, change in volume or form to produce a disruptive force that opposes the efficiency of the binder/s causing the compressed table to break apart. They belong to different morphological classes and possess different functionality properties. A non-limiting list of the different classes of disintegrants or mixtures thereof which can be used in the formulations of the present invention is given below:

(1) natural starches, such as maize starch, potato starch etc., directly compressible starches such as starch 1500, modified starches such as carboxymethylstarches and sodium starch glycolate which are available as PRIMOJEL® and EXPLOTAB® and EXPLOSOL® and starch derivatives such as amylose.

(2) cross-linked polyvinylpyrrolidones, e.g. crospovidones available as e.g. POLYPLASDONE XL® and KOLLIDON XL®.

(3) modified celluloses such as cross-linked sodium carboxymethylcelluloses available as, e.g., AC-DI-SOL®, PRIMELLOSE®, PHARMACEL XL®, EXPLOCEL®, and NYMCEL ZSX®;

(4) Alginic acid and sodium alginate.

(5) Microcrystalline cellulose, e.g. AVICEL®, PHARMACEL®, EMCOCELL®, VIVAPUR®.

(6) Methacrylic acid-divinylbenzene copolymer salts available as eg AMBERLITE® IRP-88.

Preferred are categories (1), (2) and (3) listed above which are known in the art as the so-called 'super' disintegrants.

Accordingly it is preferred that the disintegrant present in the formulations of this invention comprises at least one super disintegrant. Particularly preferred are cross-linked PVPs.

Although microcrystalline cellulose is often regarded as a weak disintegrant, it is also used in preparing tablets because of its properties as a filler and plasticising agent and therefore can be regarded as a substantially water insoluble excipient.

We have found the presence of microcrystalline cellulose is particularly advantageous in achieving superior tablet characteristics because of its plasticising properties. Accordingly in yet a further aspect, this invention provides a tablet as defined above which further comprises microcrystalline cellulose.

The multiparticulate fast disintegrating tablets of this invention are obtained by standard tableting procedures such as by forming a dry mixture which comprises all of the above mentioned components prior to direct compression in punches/dies.

Substantially water insoluble inorganic excipients include for example, water insoluble fillers and/or diluents, eg salts such as dibasic calcium phosphate, calcium phosphate tribasic, calcium sulfate and dicalcium sulfate. Particularly preferred is dibasic calcium phosphate (hydrated or anhydrous) with the anhydrous form being most preferred. Advantageously the particle size of the water insoluble inorganic excipient is such that at least 35% of the particles are larger than 75 $\mu$m. Preferably at least 45% of the particles are larger than 75 $\mu$m. Most preferably at least 80% of the particles are larger than 75 $\mu$m.

Substantially water soluble components that may be used in the present invention include for example, compression sugars or soluble fillers (e.g. lactose, sucrose, amylose, dextrose, mannitol, inositol etc.), flavouring agents, sweeteners (e.g. aspartame, saccharine etc.), pH adjusting agents (e.g. fumaric acid, citric acid, sodium acetate etc.), binders (e.g. polyethylene glycols, soluble hydroxyalkylcelluloses, polyvinylpyrrolidone, gelatins, natural gums-etc.), surfactants (e.g. sorbitan esters, docusate sodium, sodium lauryl sulphate, cetriride etc.), soluble inorganic salts (eg sodium carbonate, sodium bicarbonate, sodium chloride etc.).

In preferred embodiments, the dry mixture of the essential components of the invention gives rise upon direct compression to fast disintegrating tablets having a disintegration time of less than 20 seconds in the oral cavity.

When preparing the fast disintegrating tablets of this invention we have found that superior tablet properties can be achieved by choosing appropriate amounts of the ingredients according to the classification shown below:

(A) substantially water insoluble components; this includes the amount of drug either coated or uncoated and the amount of insoluble excipients including the insoluble inorganic salt used as filler/diluent, (eg di- or tri-basic calcium phosphate) organic filler (eg microcyrstalline cellulose) or water insoluble lubricant (eg magnesium stearate, sodium stearyl fumarate, stearic acid or glyceryl behenate) and glidant (eg talc, silicon dioxide etc).

(B) substantially soluble components, eg the amount of compression sugars (eg lactose, flavouring agents, sweeteners (aspartame), binders (eg PVP) and surfactants etc.

(C) disintegrant, especially super-disintegrant such as maize starch or modified starches, cross-linked polyvinyl pyrrolidone or sodium carboxymethylcellulose.

We have also found that for constant ratios of ingredients (A) and (B) increasing the amount of disintegrant generally gives poorer friability values and increased disintegation times. In view of this the amount of super disintegrant (C) should not be excessive and is therefore preferably in the range 0.5 to 30%, most preferably 1–20%, most preferably 2–15% by weight of the tablet.

The amount of the substantially water insoluble components (A) can be for example in the range 50–99.5% of the formulation by weight, eg. 60–99.5%, preferably 70–95%, most preferably about 72–92% by weight.

The amount of substantially water insoluble inorganic excipient may be for example in the range 2–40% of the formulation by weight, eg 2–35%, preferably 4–25%, most preferably about 6–18% by weight. As the amount of insoluble component decreases we have found that the disintegration time increases. Accordingly where the active ingredient is very potent, disintegration time is optimised by compensating for the absence of insoluble drug or insoluble microencapsulated drug (where the drug can be soluble or insoluble) by including an insoluble filler, eg microcrystalline cellulose, silicon dioxide or by increasing the amount of insoluble inorganic excipient, eg calcium salt such as dibasic calcium phosphate. Advantageously the amount of coated or uncoated active relative to substantially water insoluble inorganic excipient is in the range 25:1 to 0.35:1; preferably 10:1 to 0.37:1; most preferably about 9:1 to 2:1.

The amount of the optional substantially water soluble component(s) (B) is for example in the range 0–25% of the formulation by weight, preferably 0–20%, most preferably about 4–16% by weight.

Microcrystalline cellulose can be present in the range up to 40% by weight of the formulation, preferably 5–30%, most preferably about 8 to 25%, eg 12–22%.

The amount of water insoluble inorganic excipient(s) relative to super disintegrant(s) can be in the range between 1:9 and 9:1; preferably in the range 1:5 to 4:1 by weight; most preferably in the range 1:2.5 to 3.6:1 by weight.

When microcrystalline cellulose is present the ratio of water-insoluble inorganic excipient to microcrystalline cellulose is preferably in the range 100:1 to 1:9 by weight.

The powder formulations of this invention are conveniently prepared using conventional procedures to ensure homogeneous mixing of the components. Tablets may be formed from such formulations by direct compression methods.

The following Examples illustrate the invention:

GENERAL PROCEDURE FOR EXAMPLES 1–14

Powder mixtures were prepared according to the general procedure given below:

The excipients (except magnesium stearate) were premixed in a polyethylene bag by manual shaking and sieved through a 700 $\mu$m screen. Microcapsules were added to the excipient mixture and mixed in a 8 liter or 1.6 liter cube using an Erweka AR400 blender (D-Heusenstamm) for 20 minutes at 20 rpm. Magnesium stearate if used was added to mixture at this stage and mixed for 5 minutes at 20 rpm. Compression was performed with a rotary tableting machine (Ronchi mod. AM13/8, I-Cinisello Balsamo), equipped with either two 12 mm or 15 mm diameter scored flat punches. Operating conditions were standardised at 20 rpm. The tableting machine was instrumented to measure compression and ejection forces with strain gauges, interfaced to a Yokogawa mod. 3655E data computer and analyser.

TABLET CHARACTERISTICS

Hardness was measured by diametral crushing on a Schleuninger mod. 6D hardness tester (CH-Solothurn). The tests were performed according to European Pharmacopoeia 1997 Section 2.9.8.

Average tablet weight and weight variation were calculated using a Mettler mod. PM460 balance (Sae Scientifica, I-Mazzo di Rho), equipped with calculator Stat Pac-M and printer GA44.

Thickness was determined using a Mitutoyo mod. 500-311 caliper (Tecnogalencia, I-Cernusco sul Naviglio).

Friability was measured by an Erweka TA friabilometer (D-Heusenstamm). The test was performed for 4 minutes using 20 tablets.

Disintegration time was determined by placing a tablet into a 2 liter beaker (14 cm diameter, 18 cm height) containing 1 liter of water at room temperature whilst continuously stirring using a helix at 100±5 rpm. The helix was placed in a fixed position just below the water surface. The completes dispersion of the tablets was considered as the end point.

EXAMPLE 1

Fast disintegrating tablets were made according to the method above using formulations having the ingredients shown in Table 1 below:

TABLE 1

| FORMULATION INGREDIENT | EXAMPLE 1 weight(mg) | COMPARATIVE EXAMPLE 1A weight(mg) |
|---|---|---|
| Ibuprofen MC | 530 | 530 |
| Aerosil 200 V | 6 | 6 |
| Avicel PH101 |  | 90 |
| Kollidon CL | 60 | 60 |
| Ac-Di-Sol | 50 | 50 |
| Dicafos C52-14* | 250 |  |
| Lactose SD |  | 160 |
| Aspartame | 25 | 25 |
| Strawberry Flavour | 15 | 15 |
| Talc | 50 | 50 |
| Magnesium stearate | 4 | 4 |
| Total tablet weight (mg) | 990 | 990 |
| Total weight/g (starting mixture) | 1980 | 1980 |

*Dicafos C52-14 = dihydrate dibasic calcium phosphate

RESULTS 15 mm Diameter Tablets

Tablets having 15 mm diameter were made from the ingredients of Example 1 with tensile strengths of 0.38 N/mm$^2$ (compression force 20 kN) and 0.47 N/mm$^2$ (compression force 25.2 kN). Disintegration times were 20±1 seconds and 21±1 seconds respectively. For comparison tablets (15 mm diameter) were also made according to Example 1A (based on Example 1 of U.S. Pat. No. 5,464,632) which differed by containing no inorganic insoluble filler/diluent. At tensile strengths of 0.39 and 0.59 N/mm$^2$ the latter produced much slower disintegration times of 40±2 seconds and 46±2 seconds respectively.

Friability values for the 15 mm diameter tablets of Example 1 were improved by compression being 4.4% (compression force 20 kN) and 1.4% (compression force 25.2 kN) for the respective formulations above.

Accordingly these results show it is possible to prepare tablets according to Formulation 1 having very good disintegration times in the order of 20 seconds. Furthermore, friability values equal to or approaching those of conventional tablets (eg 2% or less) can be routinely produced by increasing the tensile strength without compromising the disintegration times.

In order to make the disintegration time faster for the comparative formulation 1A the compression force to prepare the tablet was lowered to 15 kN. However although this resulted in a disintegration time of 33±6 seconds, the tablet's integrity was weakened as evidenced by the increase in friability value to 4.6%.

12 mm Diameter Tablets

When the formulations in TABLE 1 above were prepared into 12 mm diameter tablets the following disintegration times/friabilities were obtained:

| FORMULATION | TENSILE STRENGTH (N/mm$^2$) | DISINTEGRATION TIME (seconds) | FRIABILITY(%) |
|---|---|---|---|
| Example 1 | 0.96 | 17 ± 1 | 0.1 |
|  | 0.52 | 15 ± 1 | 0.5 |
| Comparative | 1.12 | 41 ± 3 | 0.1 |
| Example 1A | 0.59 | 31 ± 2 | 0.2 |
|  | 0.41 | 26 ± 1 | 1.6 |

These results show the formulation of the present invention is suitable for producing very rapidly disintegrating tablets with friabilities in the range of conventional tablets that not only disintegrate more rapidly than the prior art but also demonstrate exceptional friability properties.

EXAMPLE 2

The following formulation was prepared using the general method described above:

TABLE 2

| FORMULATION INGREDIENT | EXAMPLE 2 weight(mg) |
|---|---|
| Ibuprofen MC | 225 |
| Avicel PH101 | 71 |
| Starch 1500 | 98 |
| Dicafos C52-14 | 71 |
| Aspartame | 20 |
| Strawberry flavour | 15 |
| Magnesium stearate | 5 |
| Total weight/mg (tablet) | 505 |
| Total weight/g (starting mixture) | 353 |

Dicafos C52-14 = dihydrate dibasic calcium phosphate

RESULTS 12 mm diameter tablets were prepared from the formulation of Example 2 at a tensile strength of 0.51 N/mm$^2$ (compression force 16.6 kN). The tablets so produced had a disintegration time of 28±1 seconds with a friability of 0.7%.

EXAMPLE 3

Formulations having the following ingredients shown in TABLE 3 below were prepared and made into 12 mm diameter tablets.

TABLE 3

| FORMULATION INGREDIENT | EXAMPLE 3 | COMPARATIVE EXAMPLE 3A |
|---|---|---|
| Ibuprofen MC | 240 | 240 |
| Aerosil 200 V | 5 | 5 |
| Avicel PH101 |  | 120 |
| Maize Starch | 7 | 7 |
| Kollidon CL | 27 | 27 |

TABLE 3-continued

| FORMULATION INGREDIENT | EXAMPLE 3 | COMPARATIVE EXAMPLE 3A |
|---|---|---|
| Dicafos C52-22* | 120 | |
| Citric Acid | 15 | 15 |
| Aspartame | 10 | 10 |
| Strawberry Flavour | 20 | 20 |
| Magnesium stearate | 15 | 15 |
| Total weight/mg (tablet) | 459 | 459 |
| Total weight/g (starting mixture) | 321 | 321 |

*Dicafos C52-22 = anhydrous dibasic calcium phosphate

RESULTS

Tablets (12 mm diameter) prepared from the formulation of Example 3 when compressed to produce a tensile strength of 0.62 N/mm$^2$ had a disintegration rate of 29±1 seconds and a friability of 0.4%.

Tablets (12 mm diameter) prepared according to the formulation of Example 3A having a tensile strength of 0.67 N/mm$^2$ showed complete disintegration only after 103±5 seconds.

Friabilities of both tablets of Examples 3 and 3A were both very good at <0.5% but in view of the slow disintegration of the Example 3A formulation this cannot be considered to constitute a rapidly disintegrating tablet.

These Examples show that the presence of dibasic calcium phosphate imparts superior disintegration properties when compared with a formulation comprising in which this component is replaced by microcrystalline cellulose.

EXAMPLE 4

A formulation was made up according to the ingredients in TABLE 4 below. Tablets were prepared having 12 mm diameter.

TABLE 4

| FORMULATION INGREDIENT | EXAMPLE 4 |
|---|---|
| Ibuprofen MC | 240 |
| Aerosil 200 V | 5 |
| Avicel PH101 | 75 |
| Maize Starch | 7 |
| Kollidon CL | 27 |
| Dicafos C52-14* (dihydrate dibasic calcium phosphate | 45 |
| Fumaric Acid | 15 |
| Aspartame | 10 |
| Strawberry Flavour | 20 |
| Pruv | 15 |
| Total weight/mg (tablet) | 459 |
| Total weight/g (starting mixture) | 321 |

RESULTS

By increasing the compression force during tablet preparation a series of tablets with increasing tensile strengths were made.

Disintegration times were found to fall below about 20 seconds at tensile strength values <0.7 N/mm$^2$. The friability value at tensile strength 0.68 was found to be 0.2% and the in vitro disintegation time was 18 seconds Comparison with the results in Example 3 above, shows that the presence of microcrystalline cellulose (Avicel PH101) in the ratio 75:45 to dibasic calcium phosphate gives a faster disintegration time than tablets containing no microcrystalline cellulose (Example 3) and also improves friability values.

EXAMPLES 5–7

To compare the disintegration efficacy of crospovidone with other disintegrants belonging to different morphological classes such as AC-DI-SOL® and maize starch, the following mixture of the components (i), (ii) and (iii) was prepared. Components (ii) and (iii) were sieved through a 700 micron screen and mixed in a blender equipped with a 18L steel cube for 20 minutes at 20 rpm. Component (i) previously sieved through a 700 micron screen, was added to the excipient mixture and mixed for 15 minutes at 20 rpm. The quali-quantitative compositions is the following:

| (i) | Ibuprofen microcapsules (cellulose acetate phthalate membrane) | 2400 g |
| (ii) | Fumaric Acid | 150 g |
| | Aspartame | 100 g |
| | Strawberry Flavour | 200 g |
| (iii) | Microcrystalline cellulose | 750 g |
| | Calcium phosphate tribasic | 450 g |
| | Compacted Silicon Dioxide | 50 g |

[Ingredients (i) and (iii) are substantially insoluble; ingredients (ii) are substantially soluble].

Samples (246 g) were taken from the starting mixture and poured into a 1.6 liter steel cube. To the samples were added 9.0 g of sodium stearyl fumarate and the following quantities of disintegrating agent:

(Example 5) 13.2 g of crospovidone (Example 6) 13.2 g of sodium croscarmellose (Example 7) 13.2 g of maize starch
  respectively, previously sieved through a 700 micron screen. Each mixture was mixed for 10 minutes at 24 rpm.

Compression was performed with a rotary tableting machine (Ronchi mod. AM 13/8), equipped with two 12 mm diameter scored flat punches. Operating conditions were standardised at 20 rpm and with respect to obtaining tablets with tensile strengths of about 0.45 to 0.55 N/mm$^2$.

Each tablet contains 240 mg of ibuprofen microcapsules corresponding to 200 mg of active.

The relevant data for the fast disintegrating tablets are shown in Table 6.

TABLE 6

Ibuprofen Disintegrating Tablets dosage: 200 mg per tablet

| Formulation | Weight (mg) | Thickness (mm) | Friability (%) | Tensile Strength (N/mm$^2$) | Disintegration Time (seconds) |
|---|---|---|---|---|---|
| Example 5 | 447 ± 5 | 3.63 ± 0.04 | 2.0 | 0.46 | 16 ± 1 |
| Example 6 | 445 ± 4 | 3.53 ± 0.04 | 0.6 | 0.54 | 31 ± 2 |
| Example 7 | 450 ± 6 | 3.50 ± 0.03 | 1.9 | 0.55 | 22 ± 1 |

The results indicate that the objectives of the present invention are met with a selection of different disintegrating agents. The use of these disintegrating agents can be successfully extended to microcapsules containing other drugs.

EXAMPLE 8

According to the general procedure described in Example 5 above, the following pharmaceutical mixture was prepared:

| (i) | Fluoxetine microcapsules (ethylcellulose membrane) | 620 g |
|---|---|---|
| (ii) | Aspartame | 90 g |
| | Strawberry Flavour | 190 g |
| (iii) | Microcrystalline cellulose | 760 g |
| | Dicalcium phosphate | 480 g |
| | Compacted Silicon Dioxide | 20 g |
| | Magnesium Stearate | 140 g |
| (iv) | Crospovidone | 250 g |
| | Maize Starch | 60 g |

[Ingredients i)+iii) are insoluble in the mouth; ii) are soluble and iv) are super disintegrants.]

Compression was performed with a rotary tableting machine (Ronchi mod. AM13/8), equipped with two 9 mm diameter scored flat punches. Operating conditions were standardised at 20 rpm and with respect to obtaining tablets with a tensile strength by using compression forces of about 4.5 kN. Each tablet having a weight of 261 mg contains 62 mg of fluoxetine microcapsules corresponding to 20 mg of active. The friability was 0.5% and the in vitro disintegration time was 17 seconds.

| (i) | Cimetidine microcapsules (ethylcellulose membrane) | 2400 g |
|---|---|---|
| (ii) | Lactose SD | 150 g |
| | Fumaric acid | 150 g |
| | Aspartame | 100 g |
| | Strawberry flavour | 190 g |
| (iii) | Microcrystalline cellulose | 760 g |
| | Dicalcium phosphate | 480 g |
| | Compacted silicon dioxide | 20 g |
| | Magnesium stearate | 140 g |
| (iv) | Crospovidone | 250 g |
| | Maize starch | 60 g |

[Ingredients (i)+(iii) are insoluble in the mouth; (ii) are soluble and (iv) are super disintegrants.]

Compression was performed with a rotary tableting machine (Ronchi mod. AM 13/8), equipped with two 12 mm diameter scored flat punches. Operating conditions were standardised at 20 rpm using compression forces of 17–20 kN to obtain tablets with a tensile strength of about 0.60 N/mm$^2$. Each tablet had a weight of 470 mg and contained 240 mg of cimetidine microcapsules corresponding to 200 mg of active. The friability value was 0.6% and the in vitro disintegration time was 22 seconds.

Examples 8 and 9 illustrate the use of a mixture of super-disintegrants.

EXAMPLES 10–14

The following formulations were prepared and made into tablets with the characterisics described in the TABLE below:

TABLE 7

| FORMULATION INGREDIENTS | EXAMPLE 10 weight (mg) | EXAMPLE 11 weight (mg) | EXAMPLE 12 weight (mg) | EXAMPLE 13 weight (mg) | EXAMPLE 14 weight (mg) |
|---|---|---|---|---|---|
| Ibuprofen Microcapsules | 240 | 240 | 240 | 240 | 240 |
| Aerosil 200 V (Silica) | 5 | 5 | 5 | 5 | 5 |
| Avicel PH101 (Cellulose) | 75 | 75 | 75 | 103 | 103 |
| Ca Phosph. Tribasic | 45 | 45 | 45 | 62 | 62 |
| Fumaric Acid | 15 | 15 | 15 | — | — |
| Aspartame | 10 | 10 | 10 | — | — |
| Strawberry Flavour | 20 | 20 | 20 | — | — |
| Crospovidone (Koll. Cl.) | 9 | 22 | 43 | 43 | 85 |
| Na Stearyl Fumarate | 15 | 15 | 15 | 15 | 15 |
| TOTAL | 434 | 447 | 468 | 468 | 510 |
| Tensile strength (N/mm$^2$) | 0.59 ± 0.05 | 0.46 ± 0.06 | 0.43 ± 0.01 | 0.38 ± 0.04 | 0.38 ± 0.05 |
| Friability (%) | 1.0 | 2.0 | 4.6 | 1.4 | 1.7 |
| Disintegrating time (secs) | 19 ± 2 | 16 ± 1 | 18 ± 2 | 22 ± 1 | 25 ± 4 |

EXAMPLE 9

2000 g of a wet granulate of cimetidine with PVP K 30 as binder, each granule having a size lower than 700 microns, was microencapsulated by phase separation process with 400 g of ethylcellulose. The microcapsules of cimetidine were dry mixed with the excipients according to the procedure described above. The following pharmaceutical mixture was prepared:

EXAMPLES 15–23

General Preparation

Powder mixture were prepared according to the general procedure given below:

The excipients (except magnesium stearate) were premixed in a polyethylene bag by manual shaking and sieved through a 700 μm screen. Microcapsules were added to the excipient mixture and mixed in a 1.6 L (or 30 L) cube using an Erweka AR400 blender for 20 minutes (or 25 minutes) at 20 rpm (or 15 rpm). Magnesium stearate, previously sieved through a 700 µm screen, was added to the mixture and mixed for 20 minutes (or 10 minutes) at 20 rpm (or 15 rpm). Compression was performed with a rotary tableting machine (Ronchi mod. AM 13.8), equipped with two 13 mm diameter biconvex (R=20 mm) punches. Operating condition were standardised at 20 rpm.

Tablet Characterisation

In vivo disintegration time was performed with 3–5 volunteers.

In vitro disintegration time was determined by placing a tablet into a 2 liter beaker 14 cm diameter, 18 cm height containing 1 liter of water at room temperature whilst continuously stirring using a helix at 100±5 rpm. The helix was placed in a fixed position just below the water surface. The complete dispersion of the tablets was considered as the end point.

Disintegration test, according to Pharrnacopeia Europoeia, was also performed.

The other tests for tablet characterisation (average tablet weight, hardness thickness and friability) are as referred to in the "Tablet Characterisation" section of Examples 1 to 14.

The following formulations (EXAMPLES 15–23) were prepared and tested:

EXAMPLE 15

| INGREDIENT | mg/TABLET |
| --- | --- |
| Ibuprofen microcapsules (cellulose acetate phthalate membrane) | 247 (active 200) |
| Maize starch | 65 |
| Sodium croscarmellose (Ac-Di-Sol ®) | 20 # |
| Citric acid | 15 |
| Saccharin | 15 |
| Strawberry flavour | 16 |
| Microcrystalline cellulose (Avicel PH112) | 55 |
| Dibasic calcium phosphate (Dicafos C52-22) | 34 |
| Silicon dioxide | 10 |
| Talc < 75 µm | 20 |
| Magnesium stearate | 13 |
| TABLET WEIGHT | 510 mg |

Tablets were made using two 13 mm diameter biconvex (R=20 mm) punches.
Characteristics:

| Hardness | 28–45 N |
| --- | --- |
| Friability | 0.3–0.6% |
| In vivo disintegration time | 20–25 seconds |
| In vitro disintegration time | 30–35 seconds |
| Disintegration according to Pharm. Eur. | <20 seconds |

Analogous characteristics were found using Primellose ® and Pharmacel XL ® (other sodium croscarmellose brands) rather than Ac-Di-Sol ®.

EXAMPLE 16

| INGREDIENT | mg/TABLET |
| --- | --- |
| Ibuprofen microcapsules (cellulose acetate phthalate membrane) | 247 (active 200) |
| Maize starch | 65 |
| Citric acid | 10 |
| Saccharin | 24 |
| Banana flavour | 12 |
| Microcrystalline cellulose (Avicel PH112) | 68 |
| Dibasic calcium phosphate (Dicafos C52-22) | 41 |
| Silicon dioxide | 10 |
| Talc < 75 µm | 20 |
| Magnesium stearate | 13 |
| TABLET WEIGHT | 510 mg |

Tablets were made using two 13 mm diameter biconvex (R=20 mm) punches.
Characteristics:

| Hardness | 38 ± 2 N |
| --- | --- |
| Friability | 0.5% |
| In vitro disintegration time | 34 ± 3 seconds |

EXAMPLE 17

| INGREDIENT | mg/TABLET |
| --- | --- |
| Ibuprofen microcapsules (cellulose acetate phthalate membrane) | 247 (active 200) |
| Sodium croscarmellose (AcDiSol ®) | 20 |
| Citric acid | 10 |
| Saccharin | 24 |
| Banana Flavour | 12 |
| Microcrystalline cellulose (Avicel PH112) | 98 |
| Dibasic calcium phosphate (Dicafos C52-22) | 56 |
| Silicon dioxide | 10 |
| Talc < 75 µm | 20 |
| Magnesium stearate | 13 |
| TABLET WEIGHT | 510 mg |

Tablets were made using two 13 mm diameter biconvex (R=20 mm) punches.
Characteristics:

| Hardness | 36 ± 2 N |
| --- | --- |
| Friability | 0.4% |
| In vitro disintegration time | 35 ± 2 seconds |

EXAMPLE 18

| INGREDIENT | mg/TABLET |
| --- | --- |
| Ibuprofen microcapsules | 247 (active 200) |
| Amberlite ® IRP 88 | 55 |
| Citric acid | 15 |
| Saccharin | 15 |
| Strawberyy Flavour | 16 |
| Microcrystalline cellulose (Avicel PH112) | 76 |
| Dibasic calcium phosphate (Dicafos C52-22) | 43 |
| Silicon dioxide | 10 |
| Talc < 75 µm | 20 |
| Magnesium stearate | 13 |
| TABLET WEIGHT | 510 mg |

Tablets were made using two 13 mm diameter biconvex (R=20 mm) punches.
Characteristics:

| | |
|---|---|
| Hardness | 30 ± 1 N |
| Friability | 0.4% |
| In vivo disintegration time | 30–40 seconds |
| In vitro disintegration time | 34 ± 2 seconds |

EXAMPLE 19

| INGREDIENT | mg/TABLET |
|---|---|
| Ibuprofen microcapsules | 247 (active 200) |
| Alginic acid (Protacid ® F-120) | 55 |
| Citric acid | 15 |
| Saccharin | 15 |
| Strawberry flavour | 16 |
| Microcrystalline cellulose (Avicel PH112) | 76 |
| Dibasic calcium phosphate (Dicafos C52-22) | 43 |
| Silicon dioxide | 10 |
| Talc < 75 μm | 20 |
| Magnesium stearate | 13 |
| TABLET WEIGHT | 510 mg |

Tablets were made using two 13 mm diameter biconvex (R=20 mm) punches.
Characteristics:

| | |
|---|---|
| Hardness | 33 ± 2 N |
| Friability | 0.4% |
| In vivo disintegration time | 40–45 seconds |
| In vitro disintegration time | 60 ± 5 seconds |

EXAMPLE 20

| INGREDIENT | mg/TABLET |
|---|---|
| Ibuprofen microcapsules (cellulose acetate phthalate membrane) | 240 (active 200) |
| Maize starch | 60 |
| Sodium croscarmellose (AcDiSol ®) | 16 |
| Sodium starch glycolate (Explotab ®) | 15 |
| Citric acid | 15 |
| Saccharin | 15 |
| Mint-Liquorice flavour | 16 |
| Microcrystalline cellulose (Avicel PH112) | 57 |
| Dibasic calcium phosphate (Dicafos C52-22) | 35 |
| Silicon dioxide | 15 |
| Talc < 75 m | 25 |
| Magnesium stearate | 11 |
| TABLET WEIGHT | 520 mg |

Characteristics:

| | |
|---|---|
| Hardness | 46 ± 2 N |
| Tensile Strength | 0.64 ± 0.03 N/mm² |
| Friability | 0.2% |
| In vivo disintegration time | 30–35 seconds |
| In vitro disintegration time | 46 ± 1 seconds |

Tablets were made using two 12.7 mm diameter flat punches

EXAMPLE 21

| INGREDIENT | mg/TABLET |
|---|---|
| Ethylcellulose coated microcapsules of active | 510 (active 450) |
| Crospovidone (Collidon CL ®) | 90 |
| Ammonium glycyrrhizinate (Glycamil A ®) | 40 |
| Aspartame | 40 |
| Fisherman mint flavour | 40 |
| Microcrystalline cellulose (Avicel PH112) | 71 |
| Dibasic calcium phosphate (Dicafos C52-22) | 60 |
| Silicon dioxide | 7 |
| Magnesium stearate | 22 |
| TABLET WEIGHT | 880 mg |

Characteristics:

| | | |
|---|---|---|
| Hardness | 40–50 N | 62 N |
| Tensile Strength | 0.35–0.42 N/mm² | 0.56 N/mm2 |
| Friability | 0.8–1.2% | 0.3% |
| In vivo disintegration time | 30–35 seconds | 35–45 seconds |
| In vitro disintegration time | <30 seconds | 40 seconds |

Tablets were made using two 16 mm diameter flat punches

EXAMPLE 22

| INGREDIENT | mg/TABLET | mg/TABLET |
|---|---|---|
| Ethylcellulose coated microcapsules | 510(active 450) | 510(active 450) |
| Crospovidone (Collidon CL ®) | 60 | 45 |
| Sodium croscarmellose (AcDiSol ®) | 25 | 28 |
| Maize starch | — | 12 |
| Ammonium glycyrrhizinate (Glycamil A ®) | 39 | 39 |
| Aspartame | 34 | 34 |
| Fisherman mint flavour | 39 | 39 |
| Microcrystalline cellulose (Avicel PH112) | 65 | 65 |
| Dibasic calcium phosphate (Dicafos C52-22) | 56 | 56 |
| Silicon dioxide | 5 | 5 |
| Magnesium stearate | 17 | 17 |
| TABLET WEIGHT | 850 mg | 850 mg |

Characteristics:

| | | |
|---|---|---|
| Hardness | 40 ± 3 N | 49 ± 3 N |
| Tensile Strength | 0.36 ± 0.03 N/mm² | 0.45 ± 0.03 N |
| Friability | 1.6% | 1.1% |
| In vivo disintegration time | 40 ± 2 seconds | 45 ± 3 seconds |
| Disintegration according to Pharm. Eur | <20 seconds | <25 seconds |

Tablets were made using two 16 mm diameter flat punches

EXAMPLE 23

| FORMULATION | EXAMPLE 23 | COMPARATIVE EXAMPLE |
|---|---|---|
| Placebo ethyl cellulose based microcapsules | 30 mg | 30 mg |
| Crospovidone (Kollidon CL) | 40 mg | 40 mg |
| Microcrystalline cellulose (Avicel PH101) | 39 mg | 20 mg |
| Lactose | — | 102 mg |
| Dibasic calcium phosphate (Dicafos C52-22) | 80 mg | — |
| Banana flavour | 2 mg | 2 mg |
| Aspartame | 10 mg | 10 mg |
| Silica | 2 mg | 2 mg |
| Gyceryl behenate (Compritol 888 ato) (lubricant) | 3 mg | 3 mg |
| Magnesium stearate | 4 mg | 4 mg |
| TABLET WEIGHT | 210 mg | 210 mg |

| | | |
|---|---|---|
| Hardness (N) | 26 | 17 |
| Tensile strength (N/mm2) | 0.62 | 0.41 |
| Friability (%) | 0.2 | 0.7 |
| In vivo disintegration time (20 subjects) | 13 ± 4 seconds | 24 ± 7 seconds |

Tablets were made using two 9 mm diameter flat punches.

What is claimed is:

1. A fast disintegrating tablet comprising a drug in a multiparticulate form, characterized in that it consists of:
   (i) substantially water insoluble components in amount of 50–99.5% by weight;
   (ii) one or more water insoluble inorganic excipients, in amount of 2–40% by weight;
   (iii) one or more disintegrants, in amount of 0.5–30% by weight; and
   (iv) one or more substantially water soluble excipients, in amount of 4–16% by weight.

2. A tablet according to claim 1, where said water insoluble inorganic excipient (ii) is a calcium salt.

3. A tablet according to claim 1, where said water insoluble inorganic excipient (ii) is selected from one or more of dibasic calcium phosphate, calcium phosphate tribasic, calcium sulfate, and dicalcium sulfate.

4. A tablet according to claim 1, where said water insoluble inorganic excipient (ii) is dibasic calcium phosphate, hydrated or anhydrous.

5. A tablet according to claim 1 in which the ratio of water-insoluble inorganic excipient(ii) to disintegrant(iii) is in the range 1:9 to 9:1 by weight.

6. A tablet according to claim 5 in which the ratio of water-insoluble inorganic excipient(ii) to disintegrant(iii) is in the range 1:5 to 4:1 by weight.

7. A tablet according to claim 6 in which the ratio of water-insoluble inorganic excipient(ii) to disintegrant(iii) is in the range 1:2.5 to 3.6:1 by weight.

8. A tablet according to claim 1 in which the disintegrating agent (iii) is a super disintegrant selected from the group consisting of a natural starch, a directly compressible starch, a modified starch, a cross-linked polyvinylpyrrolidone, a modified cellulose and combinations thereof.

9. A tablet according to claim 1 in which the substantially water soluble excipient (iv) when present is selected from the group consisting of a compression sugar or soluble filler, flavouring agents, sweeteners, a pH adjusting agent a binder, a surfactant, a soluble inorganic salt and combinations thereof.

10. A tablet according to claim 1 in which the drug has a particle size distribution ranging from approximately 20 to about 1000 microns.

11. A tablet according to claim 10 in which the maximum particle size is lower than about 700 microns.

12. A process for preparing a tablet according to claim 1 which comprises homogeneously mixing the ingredients in the required amount and applying direct compression to the formulation to produce a tablet.

13. A tablet according to claim 8, where the super disintegrant is a cross-linked polyvinylpyrrolidone.

14. A tablet according to claim 2, where said disintegrant is a cross-linked polyvinylpyrrolidone.

* * * * *

UNITED STATES PATENT AND TRADEMARK OFFICE
CERTIFICATE OF CORRECTION

| | | |
|---|---|---|
| PATENT NO. | : 6,596,311 B1 | Page 1 of 1 |
| APPLICATION NO. | : 09/623651 | |
| DATED | : July 22, 2003 | |
| INVENTOR(S) | : Luca Dobetti | |

It is certified that error appears in the above-identified patent and that said Letters Patent is hereby corrected as shown below:

At column 18 line 43, add the following claims and on title page change "14 claims" to --16 claims--.

-- 15. A tablet according to claim 18, wherein the ratio of water-insoluble inorganic excipient (ii) to disintegrant (iii) is in the range of 1:5 to 4:1 by weight --.

-- 16. A fast disintegrating tablet comprising a drug in multiparticulate form, characterized in that it consists of:

(i)    substantially water insoluble components in an amount of 50-90.5% by weight;

(ii)    one or more water insoluble inorganic excipients, in am amount of 2-40% by weight; and (iii)    one or more disintegrants, in am amount of 0.5-30% by weight.--

Signed and Sealed this

Twenty-seventh Day of February, 2007

JON W. DUDAS
*Director of the United States Patent and Trademark Office*